United States Patent [19]

Castrogiovanni et al.

[11] Patent Number: 5,102,654

[45] Date of Patent: Apr. 7, 1992

[54] NAIL ENAMEL EMULSION LACQUER COMPRISING A WATER PHASE AND A LACQUER PHASE

[75] Inventors: Anthony Castrogiovanni, Belford; Robert W. Sandewicz, Spotswood, both of N.J.; Cecilia Benedicto, Plainview, N.Y.

[73] Assignee: Revlon, Inc., New York, N.Y.

[21] Appl. No.: 710,486

[22] Filed: Jun. 5, 1991

Related U.S. Application Data

[63] Continuation of Ser. No. 521,887, Apr. 18, 1990, abandoned.

[51] Int. Cl.⁵ .............................................. A61K 7/043
[52] U.S. Cl. ....................................... 424/61; 514/938
[58] Field of Search ............................................ 424/61

[56] References Cited

U.S. PATENT DOCUMENTS

| | | | |
|---|---|---|---|
| 4,032,464 | 6/1977 | Mausher | 424/61 |
| 4,363,796 | 12/1982 | Bouillon | 424/61 |
| 4,649,045 | 3/1987 | Gaske | 424/61 |
| 4,666,709 | 5/1987 | Jankewitz | 424/61 |
| 4,712,571 | 12/1987 | Remz | 424/61 |
| 4,801,331 | 1/1989 | Marase | 424/61 |
| 4,820,509 | 4/1989 | Yamazaki | 424/61 |
| 4,897,261 | 1/1990 | Yamazaki | 424/61 |

Primary Examiner—Thurman K. Page
Assistant Examiner—D. Colucci
Attorney, Agent, or Firm—Julie Blackburn

[57] ABSTRACT

A single phase emulsion nail enamel for coating and hydrating human nails as well as a method for coating and hydrating human nails with the composition of the invention.

2 Claims, No Drawings

NAIL ENAMEL EMULSION LACQUER COMPRISING A WATER PHASE AND A LACQUER PHASE

This is a continuation of copending application Ser. No. 07/521,887 filed on Apr. 18, 1990 now abandoned.

TECHNICAL FIELD

The field of the invention is related to emulsion nail lacquers containing an aqueous phase.

BACKGROUND OF THE INVENTION

Nail enamels are traditionally anhydrous products. If any water is present at all in the traditional enamel it is usually due to slight contamination of the raw materials during manufacture or storage.

Proper hydration of human nails is very important to nail physiology. When nails become dehydrated, for example due to harsh environmental conditions or the use of nail enamel removers, they frequently crack, split, or peel more readily. There is thus a need for nail enamels which do not dehydrate the nails.

U.S Pat. No. 4,402,935 discloses a nail polish composition which contains water and urea to impart moisture to the nail. Polyvinyl butyral resin is used to harden the composition and increase adhesion to the nail. Urea is potentially irritating to skin and surrounding tissues, however, so it is not ideally suited to imparting moisture to the nail.

U.S. Pat. No. 3,034,965 discloses a nail treatment composition containing water, however the composition is not a nail lacquer but functions instead as a base which is used to treat nails prior to the application of polish. It has no coating or lacquer phase.

U.S. Pat. No. 4,158,053 discloses aqueous emulsion polymers suitable for nail lacquers which are formed as a result of polymerization of certain monomers in an aqueous medium. The polymerization of monomers in aqueous media results in a very slow drying lacquer since the hardening i.e. polymerization, depends on the evaporation of water rather than the much more rapid evaporation of volatile solvents. Furthermore, this preparation does not contain nitrocellulose which has a great affinity for water.

U.S. Pat. No. 4,897,261 is directed to a nail enamel composition containing water and a water soluble or oil soluble polymer in addition to the lacquer phase.

SUMMARY OF THE INVENTION

The invention is directed to a delete nail enamel emulsion composition for coating and hydrating human nails containing a water phase comprising about 1-30% water and about 0.1-10% of a nonionic surfactant; and a lacquer phase comprising about 5-25% nitrocellulose, about 10-70% of an organic solvent, about 2-15% of a $C_{1-6}$ organic alcohol, about 0.5-10% of a resin, and about 0.1-10% of a plasticizer.

The invention is also directed to a method for coating and hydrating human nails comprising applying a nail enamel emulsion composition containing a water phase comprising about 1-30% water and about 0.1-10% of a nonionic surfactant; and a lacquer phase, comprising about 5-25% nitrocellulose, about 10-70% of an organic solvent, about 2-15% of a $C_{1-6}$ organic alcohol, about 0.5-10% of a resin, and about 0.1-10% of a plasticizer.

DETAILED DESCRIPTION

The efficacy of the instant composition is based upon the affinity of water for nitrocellulose. When the emulsion of the invention is applied to human nails the water adheres to the nitrocellulose. The emulsion dries to form a hard coat through the rapid evaporation of volatile solvents leaving the nitrocellulose/water matrix which in turn leaves water available to hydrate the nail. The amount of water absorbed by the nail will be in direct proportion to its degree of dehydration. The nail enamel composition of the invention is useful for therapeutic as well as cosmetic purposes, and continued use of the composition will temper the effects of dehydrated nails.

The composition essentially consists of two phases: a water phase and a lacquer phase. The water phase comprises about 1 to 30% water and abut 0.1 to 10% of a nonionic surfactant. Any type of water is suitable although deionized water is preferable. A wide variety of nonionic surfactants are suitable. Generally they may be alcohol-ethylene oxide condensates, fatty acid ethylene oxide condensates, phenol-ethylene oxide condensates, modified alkyl resins, or sorbitan fatty acid adducts such as sorbitan trioleate, sorbitan sesquioleate, oleth, nonoxynol, methoxypropanol, sodium dioctyl sulfosuccinate, ethoxylated alkyl phenol, or Polysorbate 20. The water phase may additionally contain water soluble colorants, suspension agents, emollients, vitamins, U.V. absorbers, or humectants. The water phase maybe prepared by separately mixing the water, and nonionic surfactant at room temperature.

The lacquer phase comprises about 5-25% nitrocellulose, about 10-70% of an organic solvent, about 2-15% of a $C_{1-6}$ organic alcohol, about 0.5-10% of a resin, and about 0.1-10% of a plasticizer. The lacquer phase may additionally contain lipophilic materials, pigments or dyes, vitamins, dispersing agents, thickeners, preservatives, moisturizers, emollients, chelating agents or U.V. absorbers. Suitable organic solvents are those generally known to be used in nail lacquers. For example, solvents used in nitrocellulose nail lacquer formulations are considered in three related categories: active solvents, couplers or latent solvents, and diluents. Active solvents are those which dissolve nitrocellulose and include ketones, esters, amides, glycol ethers, and niotroparaffins. Couplers or latent solvents are generally alcohols. In and of themselves they are not solvents for nitrocellulose but when used in conjunction with active solvents they increase their strength. The alcohol couples with the ester resulting in a synergism. Depending on the percentage of alcohol using the flow of nail enamel can be improved. Diluents are another component of the solvent system are referred to as nonsolvents for nitrocellulose and they are used to stabilize the viscosity of nail lacquers. Aromatic or aliphatic hydrocarbons, such as toluene, xylene, and heptane are most frequently used. Representative organic solvents are one or more of ethyl acetate, butyl acetate, toluene, xylene, dipropylene glycol mono-N-butyl ether, ethyl lactate, amyl acetate, acetone, 2-methoxyethyl acetate, methyl ethyl ketone, methylisobutyl-ketone, methyl acetate, PPG-2 butyl ether, etc. The preferred solvents are ethyl acetate, N-butyl acetate, toluene, dipropylene glycol mono-N-butyl ether, or PPG-2 butyl ether. The lacquer phase further comprises about 5-15% of a $C_{1-6}$ organic alcohol which acts as a coupler or latent solvent in the solvent system. Any alcohol with a carbon backbone in the $C_{1-6}$ range is suitable. Organic alcohols with a carbon backbone in the $C_{2-4}$ range are preferred for example isopropanol, butyl alcohol, ethyl alcohol, or n-propanol, methoxypropanol, but particularly isopropanol.

About 0.5-10% resin is necessary in the lacquer phase. Suitable resins are acrylics, acrylates, polyester, polyurethane, epoxy, urea aldehyde, toluenesulfonamide/formaldehyde resin, etc. Preferably sucrose acetate isobutyrate, sucrose benzoate, sucrose acetate or toluene sulfonamide/formaldehyde resin is used. A wide variety of plasticizers well known to those skilled in the art are suitable for the lacquer phase in the concentration range of about 0.25-10%. Preferably the plasticizer is camphor, dibutyl phthalate, tricresyl phosphate, butyl phthalyl, butyl glycolate, dioctyl phthalate, triphenyl phosphate, dibutyl ethyl phthalate, acetyl tributyl citrate, glyceryl triacetate, glyceryl tribenzoate, dicyclohexyl phthalate, butyl benzyl phthalate, PPG-2 dibenzoate, ethylene glycol dibenzoate, or castor oil. In the preferred embodiment of the invention dibutyl phthalate is used. There are a wide variety of nitrocelluloses which may be used in the lacquer phase which comprises about 5-25% nitrocellulose. The ½ second RD Nitrocelluslose and the ¼ second RS Nitrocellulose work best and are preferred. The lacquer phase may additionally contain one or more colorants or pigments, emollients, vitamins, moisturizing agents, thickeners, preservatives, antifoam agents or chelators. Preferably the composition additionally contains one or more of: 0.001-0.500% colorant, 0.001-0.500% moisturizer, 0.001-0.500% emollient, 0.001-0.500% vitamin, or 0.05-1.5% U.V. absorber.

The preferred colorants are FD&C Blue #1 or D&C Green #6. The preferred moisturizers are licorice extract, methoxypropylgluconamide, dimethicone, evening primrose oil, or linoleic acid. The preferred emollients are phytantriol, tocopherol acetate. The preferred U.V. absorbers are etocrylene or benzophenone. A variety of vitamins are preferred including retinol, calciferol, calcium pantothenate, or panthenol. The lacquer phase is mixed separately at room temperature by agitation with a simple mixer.

Examples of optional additives include but are not limited to those set forth below:

Colorants
  Lakes of D&C Red 21, D&C Red 27, D&C Red #6, D&C Red #7, D&C Red #34, D&C Red #33
  D&C orange #5
  D&C green #5 & #6
  FD&C blue #1
  D&C yellow #5 & #6
  D&C violet #2
  titanium oxides
  iron oxide
  carmine
  mica
  titanated mica
  guanine
  bismuth oxychloride
  powdered aluminum
  silver powder
Moisturizing Agents
  methoxypropylgluconamide
  dimethicone
  evening primrose oil
  linoleic acid
  licorice extract
  propylene glycol
  alkyl glycosides
  botanical extracts
  hyaluronic acid and salts thereof
  pyrollidone carboxylates
Vitamins
  calcium pantothenate
  panthenol
  Vitamin A (retinol)
  Vitamin D (calciferol)
  Vitamin E
U.V. Absorbers
  octocrylene
  benzophenone-1
  etocrylene
  4-dodecyloxy-2-hydroxy benzophenone
  benzophenone-3
  drometrizole
Emollients
  tocopherol acetate
  phytantriol
  lanolin
  mineral oils
  isopropyl palmitate
  isopropyl myristate
Thickeners
  organo modified montmorillonite clays
  silica
  acrylic acid polymers The emulsion is then made by mixing about 5-30% of the water phase with about 70-95% of the lacquer phase by simple mixing at room temperature. It is important to note that if the percentage of water phase is too great the mixture will not form an emulsion. Generally up to about 30% water will yield an emulsion which does not separate on standing. After combining the two phases the resultant product is an opaque, single phase liquid with a viscosity of about 1000 cps at 25° C. The writeoffs of films cast from this product are clear, transparent and lustrous. As mentioned previously it is important to note that the composition has been engineered so that the mechanism by which the product dries is through the evaporation of volatile solvent. This is in contrast to many other emulsified coating products which form a film by coalescence. The volatile solvent drying mechanism provides for nail hydration and is an essential feature of the invention.

The invention is also directed to a method for coating and hydrating human nails comprising applying a single phase nail enamel emulsion composition containing a water phase comprising about 1-30% water and about 1-10% of a nonionic surfactant; and a lacquer phase comprising about 5-25% nitrocellulose, about 10-40% of an organic solvent, about 5-15% of a $C_{1-6}$ organic alcohol, about 0.5-10% of a resin, and about 0.25-10% of a plasticizer. The nail enamel composition of the invention may be used for therapeutic as well as aesthetic purposes and constitutes a very effective treatment regimen for therapy of brittle, dehydrated nails. Repeated use of the composition will assist in eliminating the nail drying effects of harsh environmental conditions, anhydrous nail lacquer, chemicals, and so forth. The invention is further described in connection with the following examples which are set forth for the purposes of illustration only. The invention includes but is not limited to the preferred embodiments set forth below.

EXAMPLE 1

A single phase emulsion nail lacquer was made by combining a water phase and a lacquer phase of the following constituents:

| | W/W % Pref'd Amt. | Pref'd Range |
|---|---|---|
| Water Phase | | |
| deionized water | 14.85 | 10-20 |
| Polysorbate 20 | 0.15 | 0.10-0.20 |
| | 15.00% | |
| Lacquer Phase | | |
| ½" RS Nitrocellulose | 6.90 | 5.-10. |
| ¼" RS Nitrocellulose | 6.90 | 5.-10. |
| Ethyl acetate | 17.60 | 10.-25. |
| N-butyl acetate | 31.00 | 25.-35. |
| isopropanol | 5.90 | 4.-10. |
| sucrose acetate isobutyrate | 2.20 | 1.-3. |
| sucrose benzoate | 3.90 | 1.-5. |
| camphor | 2.10 | 1.50-3.0 |
| dibutyl phthalate | 4.25 | 3.-5. |
| dipropylene glycol mono-N-butyl ether | 4.25 | 3.-5. |
| | 85.00% | |

The water phase comprised 15% of the final emulsion.

EXAMPLE 2

A single phase emulsion nail lacquer was made by combining a water phase and a lacquer phase of the following constituents:

| | W/W % Pref'd Amt. | Pref'd Range |
|---|---|---|
| Water Phase | | |
| water | 10.00 | 5.-15. |
| sorbitan trioleate | 0.75 | 0.1-2.0 |
| | 10.75% | |
| Lacquer Phase | | |
| nitrocellulose, dry | 10.00 | 5.-15. |
| isopropyl alcohol | 4.50 | 2.-8. |
| acetyl tributyl citrate | 5.00 | 2.-8. |
| sucrose benzoate | 9.50 | 5.-12. |
| benzophenone-1, dry | 0.25 | 0.1-0.4 |
| ethyl acetate | 60.00 | 50.-70. |
| | 90.25% | |

The final emulsion contained 10.75% water phase and 90.25% lacquer phase.

EXAMPLE 3

A single phase nail emulsion was made by combining a water phase and a lacquer phase of the following constituents:

| | W/W % Pref'd Amt. | Pref'd Range |
|---|---|---|
| Water Phase | | |
| water | 7.25 | 5-10 |
| Oleth-2 | 0.50 | 0.1-1.0 |
| | 7.75% | |
| Lacquer Phase | | |
| nitrocellulose | 12.50 | 10-15 |
| glyceryl triacetate | 7.00 | 5-10 |
| toluene sulfonfamide/formaldehyde resin | 5.00 | 3-8 |
| etocrylene | 0.75 | 0.1-1.0 |
| N-butyl acetate | 30.25 | 25-35 |
| ethyl acetate | 30.00 | 25-35 |
| isopropyl alcohol | 7.50 | 5-10 |
| | 92.25% | |

The final emulsion contained about 7.75% water.

EXAMPLE 4

A nail enamel emulsion was made by mixing a lacquer phase and a water phase of the following constituents:

| | W/W % Pref'd Amt. | Pref'd Range |
|---|---|---|
| Water Phase | | |
| water | 25.00 | 20-30 |
| nonoxynol | 0.50 | 0.1-1.0 |
| sorbitan sesquioleate | 1.50 | 1.0-2.0 |
| FD & C Blue #1 | 0.01 | 0.001-0.05 |
| | 27.01% | |
| Lacquer Phase | | |
| nitrocellulose, dry | 11.50 | 10-15 |
| isopropyl alcohol | 8.00 | 5-10 |
| N-butyl acetate | 35.24 | 30-40 |
| ethyl acetate | 2.50 | 2-3 |
| methoxypropanol | 3.00 | 1-5 |
| acrylates copolymer | 3.50 | 3-4 |
| toluene | 0.25 | 0.1-0.5 |
| benzophenone-1 | 0.25 | 0.1-0.5 |
| dibutyl phthalate | 5.50 | 2-7 |

EXAMPLE 6

| | W/W % Pref'd Amt. | Pref'd Range |
|---|---|---|
| Water Phase | | |
| water | 6.800 | 5-10 |
| panthenol | .009 | .001-.015 |
| sorbitan trioleate | .986 | .100-1.500 |
| 0.2% Green | .150 | .010-.500 |
| calcium pantothenate | .001 | .0005-.0100 |
| dioctyl sodium sulfosuccinate | .055 | .0100-.1000 |
| Lacquer Phase | | |
| nitrocellulose solution (¼" RS nitrocellulose, 24.5% solids, 43% butyl acetate, 22% ethyl acetate) | 37.200 | 30-45 |
| ethyl acetate | 20.616 | 15-25 |
| butyl acetate | 17.900 | 10-25 |
| methoxy propanol | 3.490 | 1-7 |
| PPG-2 butyl ether | 1.160 | 0.5-5 |
| dibutyl phthalate | 3.250 | 0.5-5 |
| sucrose benzoate/sucrose acetate isobutyrate | 7.440 | 3-12 |
| etocrylene | .744 | .1-1.5 |
| tocopherol acetate | .009 | .001-.015 |
| isopropanol | .160 | .050-.500 |
| retinol & calciferol | .009 | .001-.015 |
| evening primrose oil and linoleic acid | .009 | .001-.015 |
| phytantriol | .009 | .001-.015 |
| dimethicone | .001 | .0005-.0100 |
| methoxypropylgluconamide | .001 | .0005-.0100 |
| licorice extract | .001 | .0005-.0100 |

EXAMPLE 5

A single phase nail emulsion was made by mixing a water phase and a lacquer phase of the following constituents:

|  | W/W % Pref'd Amt. | Pref'd Range |
| --- | --- | --- |
| Water Phase | | |
| water | 8.50 | 5–12 |
| sorbitan trioleate | 1.00 | 0.1–2.0 |
| | 9.50% | |
| Lacquer Phase | | |
| nitrocellulose | 10.00 | 5–15 |
| N-butyl acetate | 28.00 | 20–30 |
| ethyl acetate | 31.00 | 25–35 |
| isopropyl alcohol | 8.00 | 5–10 |
| sucrose benzoate | 4.50 | 3–10 |
| sucrose acetate isobutyrate | 1.50 | 1.0–2.0 |
| dibutyl phthalate | 3.00 | 1–5 |
| methoxypropanol | 4.50 | 3–6 |
| | 90.50% | |

We claim:

1. A nail enamel emulsion lacquer comprising about

|  | w/w % |
| --- | --- |
| Water Phase | |
| water | 5–10 |
| panthenol | .001–.015 |
| sorbitan trioleate | .100–1.500 |
| D&C green #6 in butyl acetate | .001–.500 |
| Ca pantothenate | .0005–.0100 |
| dioctyl sodium sulfosuccinate | .0100–.1000 |
| Lacquer Phase | |
| nitrocellulose solution | 30–45 |
| ethyl acetate | 15–25 |
| butyl acetate | 10–25 |
| methoxypropanol | 1–7 |
| PPG-2 butyl ether | 0.5–5 |
| dibutyl phthalate | 0.5–5 |
| sucrose benzoate/sucrose acetate isobutyrate | 3–12 |
| etocrylene | .1–1.5 |
| tocopherol acetate | .001–.015 |
| isopropanol | .050–.500 |
| retinol and calciferol | .001–.015 |
| evening primrose oil and linoleic acid | .001–.015 |
| phytantriol | .001–.015 |
| dimethicone | .0005–.0100 |
| methoxypropylgluconamide | .0005–.0100 |
| licorice extract | .0005–.0100 |

2. The composition of claim 1 containing about

|  | W/W % |
| --- | --- |
| Water Phase | |
| water | 6.800 |
| panthenol | .009 |
| sorbitan trioleate | .986 |
| D & C Green #6 in butyl acetate | .150 |
| Ca pantothenate | .001 |
| dioctyl sodium sulfosuccinate | .055 |
| Lacquer Phase | |
| nitrocellulose solution | 37.200 |
| ethyl acetate | 20.616 |
| butyl acetate | 17.900 |
| methoxypropanol | 3.490 |
| PPG-2 butyl ether | 0.5–5 |
| dibutyl phthalate | 3.250 |
| sucrose benzoate/sucrose acetate isobutyrate | 7.440 |
| etocrylene | .744 |
| tocopherol acetate | .009 |
| isopropanol | .160 |
| retinol and calciferol | .009 |
| evening primrose oil and linoleic acid | .009 |
| phytantriol | .009 |
| dimethicone | .001 |
| methoxypropylgluconamide | .001 |
| licorice extract | .001 |

* * * * *